US007002036B2

(12) United States Patent
Chorghade et al.

(10) Patent No.: US 7,002,036 B2
(45) Date of Patent: Feb. 21, 2006

(54) SYNTHESIS OF 2-ALKYL AMINO ACIDS

(75) Inventors: Mukund S. Chorghade, Natick, MA (US); Mukund K. Gurjar, Pune Maharashtra (IN); Debendra K. Mohapatra, Orissa (IN)

(73) Assignee: Genzyme Corporation, Cambridge, MA (US)

( * ) Notice: Subject to any disclaimer, the term of this patent is extended or adjusted under 35 U.S.C. 154(b) by 23 days.

(21) Appl. No.: 10/438,770

(22) Filed: May 15, 2003

(65) Prior Publication Data

US 2004/0024224 A1 Feb. 5, 2004

Related U.S. Application Data

(60) Provisional application No. 60/392,833, filed on Jun. 27, 2002, provisional application No. 60/381,021, filed on May 15, 2002, provisional application No. 60/381,017, filed on May 15, 2002, provisional application No. 60/381,013, filed on May 15, 2002, provisional application No. 60/381,012, filed on May 15, 2002, provisional application No. 60/380,910, filed on May 15, 2002, provisional application No. 60/380,909, filed on May 15, 2002, provisional application No. 60/380,903, filed on May 15, 2002, provisional application No. 60/380,895, filed on May 15, 2002, provisional application No. 60/380,894, filed on May 15, 2002, provisional application No. 60/380,880, filed on May 15, 2002, provisional application No. 60/380,878, filed on May 15, 2002.

(51) Int. Cl.
*C07C 34/00* (2006.01)

(52) U.S. Cl. .............................. 560/9; 560/12; 560/19
(58) Field of Classification Search ............... 560/9, 560/12, 19; 548/968, 966
See application file for complete search history.

(56) References Cited

U.S. PATENT DOCUMENTS

| | | | |
|---|---|---|---|
| 4,406,905 A | 9/1983 | Zähner et al. | |
| 5,554,753 A | 9/1996 | O'Donnell et al. | |
| 5,840,739 A | 11/1998 | Bergeron, Jr. | |
| 5,872,259 A | 2/1999 | Reuter | |
| 5,929,232 A | 7/1999 | Jacobsen et al. | |
| 6,083,966 A | 7/2000 | Bergeron, Jr. | |
| 6,159,983 A | 12/2000 | Bergeron, Jr. | |
| 6,383,233 B1 | 5/2002 | Reuter | |
| 6,428,583 B1 | 8/2002 | Reuter | |
| 6,521,652 B1 | 2/2003 | Bergeron | |
| 6,525,080 B1 | 2/2003 | Bergeron | |
| 6,559,315 B1 | 5/2003 | Bergeron | |
| 2003/0088105 A1 | 5/2003 | Krich et al. | |
| 2003/0220504 A1 | 11/2003 | Chorghade et al. | |
| 2003/0225287 A1 | 12/2003 | Chorghade et al. | |
| 2003/0229231 A1 | 12/2003 | Chorghade et al. | |
| 2003/0236404 A1 | 12/2003 | Gimi et al. | |
| 2003/0236426 A1 | 12/2003 | Chorghade et al. | |
| 2003/0236434 A1 | 12/2003 | Gimi et al. | |
| 2003/0236435 A1 | 12/2003 | Gimi et al. | |
| 2004/0002613 A1 | 1/2004 | Chorghade et al. | |
| 2004/0006224 A1 | 1/2004 | Chorghade et al. | |

FOREIGN PATENT DOCUMENTS

| | | |
|---|---|---|
| DE | 20 20 866 A | 11/1971 |
| DE | 30 02 989 A1 | 7/1981 |
| EP | 1 302 467 A2 | 4/2003 |
| GB | 1 292 170 | 10/1972 |
| WO | WO 94/11367 | 5/1994 |
| WO | WO 97/36885 | 10/1997 |
| WO | WO 00/01670 | 1/2000 |
| WO | WO 00/12493 A1 | 3/2000 |
| WO | WO 00/16763 | 3/2000 |

OTHER PUBLICATIONS

Bergeron, R., et al., "Desazadesmethyldesferrithiocin Analogues as Orally Effective Iron Chelators," *J. Med. Chem.*, 42:95-108 (1999).

Bergeron, R. et al., "The Desferrithiocin Pharmacophore," *J. Med. Chem.*, 37:1411-1417 (1994).

Bergeron, R. et al., "Effects of C-4 Stereochemistry and C-4 Hydroxylation on the Iron Clearing Efficiency and Toxicity of Desferrithiocin Analogues," *J. Med. Chem.*, 42:2432-2440 (1999).

Bergeron, R. et al., "Synthesis and Biological Evaluation of Naphthyldesferrithiocin Iron Chelators," *J. Med. Chem.*, 39:1575-1581 (1996).

Bergeron, R. et al., "Evaluation of Desferrithiocin and Its Synthetic Analogues as Orally Effective Iron Chelators," *J. Med. Chem.*, 34:2072-2078 (1991).

Bergeron, R. et al., "Evaluation of the Desferrithiocin Pharmacophore as a Vector for Hydroxamates," *J. Med. Chem.*, 42:2881-2886 (1999).

Bergeron, R. et al., "An Investigation of Desferrithiocin Metabolism," *J. Med. Chem.*, 37:2889-2895 (1994).

Bergeron, R. et al., "A Comparative Study of the Iron-Clearing Properties of Desferrithiocin Analogues with Desferrioxamine B in a *Cebus* Monkey Model," *Blood*, 81(8):2166-2173 (1993).

(Continued)

*Primary Examiner*—Taofiq Solola
*Assistant Examiner*—Robert Shiao
(74) *Attorney, Agent, or Firm*—Hamilton, Brook, Smith and Reynolds, P.C.

(57) ABSTRACT

Non-natural amino acids such as 2-alkylated amino acids allow for the synthesis of a wider variety of peptidal and non-peptidal pharmaceutically active agents. A method of preparing a 2-alkyl amino acid involves a Michael-type addition of a nucleophile to a dialkyl 2-methylidenylpropan-1,3-dioate and the conversion of a ester moiety into an amino moiety. The present invention also discloses a method of preparing a class of iron chelating agents related to desferrithiocin, all of which contain a thiazoline ring. In this method, an aryl nitrile or imidate is condensed with cysteine, a 2-alkyl cysteine, or a cysteine ester.

17 Claims, No Drawings

OTHER PUBLICATIONS

Bergeron, R., et al., "Pharmacokinetics of Orally Administered Desferrithiocin Analogs in *Cebus Apella* Primates," *Drug Metabolism and Disposition*, 27(12):1496-1498 (1999).

"Aliphatic Nucleophilic Substitution," In *Advanced Organic Chemistry*, by Jerry March (Wiley Interscience), Ch. 10, pp. 433-434 (1992).

"Eliminations," In *Advanced Organic Chemistry*, by Jerry March (Wiley Interscience), Ch. 17, pp. 1012-1014 (1992).

Mulqueen, G. C., et al., "Synthesis of the Thiazoline-based Siderophore (S)-Desferrithiocin," *Tetrahedron*, 49(24): 5359-5364 (1993).

O'Donnell, M. J., et al., "α-Methyl Amino Acids by Catalytic Phase-Transfer Aklylations," *Tetrahedron Letters*, 23(41):4259-4262 (1982).

Ehrler, Juerg, and Farooq, Saleem, "Total Synthesis of Thiangazole," *Synlett*, 702-704 (1994).

Kishore, V., et al., "Synthesis of α-Poly-[$N^\epsilon$-(2-aryl-$\Delta^2$-thiazoline-4-carbonyl)-ʟ-lysines] With Antiviral Activity," *Indian Journal of Chemistry 15B*: 255-257 (1977).

Zamri, Adel, and Abdallah, Mohamed A., "An Improved Stereocontrolled Synthesis of Pyochelin, Siderophore of *Pseudomonas aeruginosa* and *Burkholderia cepacia*," *Tetrahedron 56:* 249-256 (2000).

SYNTHESIS OF 2-ALKYL AMINO ACIDS

RELATED APPLICATIONS

This application claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. This application also claims the benefit of U.S. Provisional Application No. 60/392,833, filed Jun. 27, 2002. The entire teachings of the above-referenced applications are incorporated herein by reference.

BACKGROUND OF THE INVENTION

Alpha-amino acids are useful starting materials in the synthesis of peptides, as well as non-peptidal, pharmaceutically active peptidomimetic agents. In order to enable the synthesis of a large number of compounds from an amino acid precursor, it is advantageous to have naturally occurring and non-naturally occurring amino acids. Non-naturally occurring amino acids typically differ from natural amino acids by their stereochemistry (e.g., enantiomers), by the addition of alkyl groups or other functionalities, or both. At this time, the enantiomers of naturally occurring amino acids are much more expensive than the naturally occurring amino acids. In addition, there are only a limited number of commercially available amino acids that are functionalized or alkylated at the alpha-carbon, and often syntheses involve the use of pyrophoric or otherwise hazardous reagents. Moreover, the syntheses are often difficult to scale up to a commercially useful quantity. Consequently, there is a need for new methodologies of producing such non-naturally occurring amino acids.

Non-naturally occurring amino acids of interest include the (R)- and (S)-isomers of 2-methylcysteine, which are used in the design of pharmaceutically active moieties. Several natural products derived from these isomers have been discovered in the past few years. These natural products include desferrithiocin, from *Streptomyces antibioticus*; as well as tantazole A, mirabazole C, and thiangazole, all from blue-green algae. These compounds have diverse biological activities ranging from iron chelation to murine solid tumor-selective cytotoxicity to inhibition of HIV-1 infection.

Desferrithiocin, deferiprone, and related compounds represent an advance in iron chelation therapy for subjects suffering from iron overload diseases. Present therapeutic agents such as desferroxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues. Unfortunately, (S)-2-methylcysteine, which is a precursor to the more active forms of desferrithiocin and related compounds, remains a synthetic challenge. Therefore, there is a need for novel methods of producing 2-methylcysteine at a reasonable cost, and means of isolating the desired enantiomer.

SUMMARY OF THE INVENTION

The present invention includes a method of preparing a compound represented by Structural Formula (I):

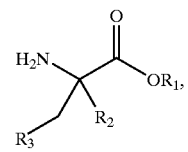

(I)

or a salt thereof;

wherein:
$R_1$ is —H or a substituted or unsubstituted alkyl group;
$R_2$ is a substituted or unsubstituted alkyl group; and
$R_3$ is —H, —SH, —OH, —$NH_2$, —$CO_2H$, —$CONH_2$, —NHC(NH)$NH_2$, a substituted or unsubstituted alkyl group, a substituted or unsubstituted cycloaliphatic group, a substituted or unsubstituted heterocyclic group, a substituted or unsubstituted aromatic group, or a substituted or unsubstituted heteroaromatic group, wherein $R_3$ optionally comprises a protecting group;

comprising the steps of:
a.) reacting a nucleophile of the formula A—$R_3$ or A—($R_3$)$_2$, with a compound represented by Structural Formula (II):

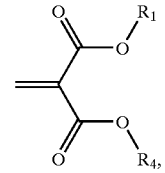

(II)

wherein:
A is —H, —Li,

—MgCl, —MgBr, or —MgI, provided that A and $R_3$ are not each —H;
$R_4$ is —H or a substituted or unsubstituted alkyl group; and
$R_1$ and $R_3$ are as defined above;
thereby forming a compound represented by Structural Formula (III):

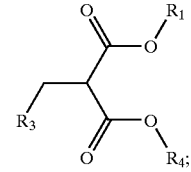

(III)

b.) reacting the product of step (a.) with one or more bases, $R_2X$, and a phase transfer catalyst,
wherein X is a leaving group; and $R_1$, $R_2$, $R_3$, and $R_4$ are as defined above;
thereby forming a compound represented by Structural Formula (IV):

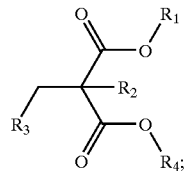

(IV)

c.) converting the product of step (b.) into a compound represented by Structural Formula (V):

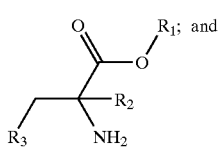

(V)

d.) optionally cleaving the protecting group of $R_3$, thereby forming the compound represented by Structural Formula (I).

In another embodiment, the present invention is a method of preparing a compound represented by Structural Formula (VII):

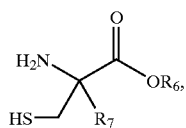

(VII)

or a salt thereof;

wherein:

$R_6$ is —H or a substituted or unsubstituted alkyl group; and $R_7$ is a substituted or unsubstituted alkyl group comprising the steps of:

a.) reacting a nucleophile, A-S-Z, with a compound represented by Structural Formula (VIII):

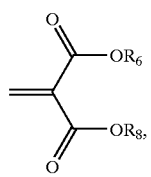

(VIII)

wherein:

A is —H;

$R_8$ is —H or a substituted or unsubstituted alkyl group;

Z is a protecting group; and $R_6$ is as defined above;

thereby forming a compound represented by Structural Formula (IX):

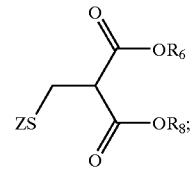

(IX)

b.) reacting the product of step (a.) with one or more bases, $R_7X$, and a phase transfer catalyst,
wherein X is a leaving group; and $R_6$, $R_7$, $R_8$, and Z are as defined above; thereby forming a compound represented by Structural Formula (X):

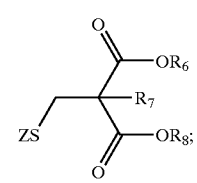

(X)

c.) converting the product of step (b.) into a compound represented by Structural Formula (XI):

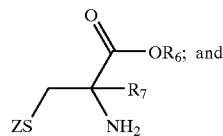

(XI)

d.) removing Z from the product of step (c.), thereby forming the compound represented by Structural Formula (VII).

Preferably, $R_1$ and $R_6$ are methyl and $R_4$ and $R_8$ are t-butyl.

The above methods can additionally comprise the step of resolving enantiomers or diastereomers of a 2-alkyl amino acid (or an ester or a salt thereof). Preferably, the method comprises isolating the (R)- and (S)-enantiomers of 2-alkyl amino acids, or esters or salts thereof.

The present invention also includes a method of preparing a compound represented by Structural Formula (XVI):

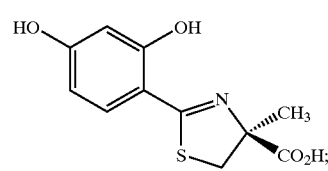

(XVI)

comprising the step of coupling (S)-2-methylcysteine or a salt thereof, as prepared by a method described herein, to 2,4-dihydroxybenzonitrile. Alternatively, an analogous compound can be synthesized by coupling 2-hydroxybenzonitrile and (S)-2-methylcysteine or a salt or an ester thereof. Similar syntheses can be conducted with other substituted benzonitriles.

Advantages of the present invention include the facile synthesis of a 2-alkyl amino acid from a dialkyl 2-methylidenylpropan-1,3-dioate. Additional advantages include the ability to prepare amino acids with a wide variety of side chains, such as preparing 2-methylcysteine. 2-Methylcysteine prepared by the method of the present invention can be coupled to 2,4-dihydroxybenzonitrile to form 4'-hydroxydesazadesferrithiocin, also referred to as 4,5-dihydro-2-(2,4-dihydroxyphenyl)-4-methylthiazole-4(S)-carboxylic acid, an iron chelating agent.

DETAILED DESCRIPTION OF THE INVENTION

A useful and efficient method of preparing 2-alkyl amino acids involves a Michael-type addition of a side chain precursor to a dialkyl 2-methylidenylpropan-1,3-dioate, followed by alkylation at the 2-position of the diester. One of the ester groups can be converted into an amino moiety, typically through a reaction with an azide.

Michael-type additions of the present reaction include reacting a nucleophile of the formula $A-R_3$ or $A-(R_3)_2$ with a dialkyl 2-methylidenylpropan-1,3-dioate, which forms a 2-substituted propan-1,3-dioate ester. Typically, when the nucleophile does not contain a metal-carbon bond, the Michael-type addition occurs in a protic solvent with either a catalytic amount of a base or a stoichiometric amount of base. When the nucleophile contains a metal-carbon bond such as a lithium-carbon, copper-carbon, or magnesium carbon, the Michael-type addition occurs under conditions where the nucleophile is stable and adds to the dialkyl 2-methylidenylpropan-1,3-dioate at the desired location. Reaction temperature is generally not important, however, the temperature can range from −50° C. to 150° C., 0° C. to 100° C., or 20° C. to 60° C. Michael additions are further described on pages 741–742 and 797–803 of "Advanced Organic Chemistry, Fourth Edition," by Jerry March, Wiley-Interscience, 1992 and references therein, all of which are incorporated by reference.

Preferred nucleophiles include nucleophiles where $R_3$ is —SH, such as $H_2S$ and $CH_3COSH$. Other suitable examples of $R_3$ include —H, —$(CH_2)_xS(CH_2)_yH$, —$(CH_2)_xO(CH_2)_yH$, —$(CH_2)_xNH(CH_2)_yH$, —$(CH_2)_xC(O)NH_2$, —$(CH_2)_xC(O)OH$, —$(CH_2)_xNHC(NH)NH_2$, a C1–C6 substituted or unsubstituted alkyl group, and aryl and heteroaryl groups such as

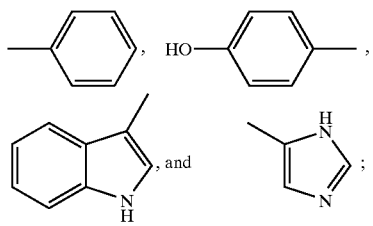

where $R_3$ optionally comprises a protecting group. The variable x can be an integer of zero or more, such as 0 to about 6, preferably 0–3, or 0 or 1. The variable y is 0 or 1.

Alkylation of a 2-substituted propan-1,3-dioate ester (forming a 2-alkyl-2-substituted propan-1,3-dioate ester) typically occurs in a protic solvent (e.g., methanol, ethanol, water, propanol, isopropanol, formic acid, acetic acid, DMF, N-ethylacetamide, formaldehyde diethyl acetal), by adding one or more bases, an alkylating agent of the formula $R_2X$ or $R_7X$, and a phase transfer catalyst. Suitable bases include alkali metal or alkaline earth metal hydroxides, alkoxides, or carbonates such as sodium hydroxide, potassium hydroxide, sodium methoxide, potassium methoxide, sodium ethoxide, potassium ethoxide, sodium carbonate, cesium carbonate, calcium carbonate and potassium carbonate, as well as sodium hexamethyl disilazide and potassium hexamethyl disilazide. Preferred alkylating agents include those where $R_2$ or $R_7$ is a C1–C4 substituted or unsubstituted alkyl group and X is a halide. Especially preferred alkylating agents include those where $R_2$ or $R_7$ is methyl or benzyl and X is a halide such as iodide. Examples of phase transfer catalysts include benzyl triethyl ammonium chloride, benzyl trimethyl ammonium chloride, benzyl tributyl ammonium chloride, tetrabutyl ammonium bromide, tetraethyl ammonium bromide, tetrabutyl ammonium hydrogen sulfate, tetramethyl ammonium iodide, tetramethyl ammonium chloride, triethylbutyl ammonium bromide, tributyl ethyl ammonium bromide, tributyl methyl ammonium chloride, 2-chloroethylamine chloride HCl, bis(2-chloroethyl)amine HCl, 2-dimethylaminoethyl chloride HCl, 2-ethylaminoethyl chloride HCl, 3-dimethylaminopropyl chloride HCl, methylamine HCl, dimethylamine HCl, trimethylamine HCl, monoethylamine HCl, diethylamine HCl, triethylamine HCl, ethanolamine HCl, diethanolamine HCl, triethanolamine HCl, cyclohexylamine HCl, dicyclohexylamine HCl, cyclohexylamine HCl, diisopropylethylamine HCl, ethylenediamine HCl, aniline HCl, methyl salicylate, ethyl salicylate, butyl salicylate amyl salicylate, isoamyl salicylate, 2-ethylsalicylate, and benzyl salicylate.

Converting a 2-alkyl-2-substituted propan-1,3-dioate ester into a 2-alkyl amino acid typically comprises a series of steps where the 2-alkyl-2-substituted propan-1,3-dioate ester is partially hydrolyzed (at $R_4$ and $R_8$) to give a free carboxylic acid, optionally converting the free carboxylic acid into an acid chloride, and the free carboxylic acid or the acid chloride is reacted with a source of azide and water to give the amino acid. Typically, hydrolysis is achieved by treating the 2-alkyl-2-substituted propan-1,3-dioate ester with acid. This hydrolysis is additionally applicable to other esters. The optional conversion into an acid chloride can be accomplished by reacting the free carboxylic acid with an agent such as $SOCl_2$, $PCl_3$, or $ClC(O)C(O)Cl$. The source of azide for an acid chloride is $MN_3$, where M is H or an alkali metal. The source of azide for a free carboxylic acid is preferably diphenylphosphoryl azide. Following reaction with a source of azide, a carboxy azide is formed, and further reaction with water and heat results in the carboxy azide rearranging into isocyanate. The isocyanate can readily be hydrolyzed to an amino moiety.

Alternatively, the above conversion can involve amidating a 2-alkyl-2-substituted propan-1,3-dioate ester. Typically, amidation involves hydrolyzing the ester to a free carboxylic acid, converting the free carboxylic acid to an acid chloride (or directly converting the ester to an acid chloride), and reacting the acid chloride with ammonia or a salt thereof. The amide can be converted to an amino moiety by reacting it with 1.) $MOR_5$ and $Y_2$ or 2.) MOY; where M is an alkali metal, $R_5$ is hydrogen, or an alkyl group such as methyl, ethyl, propyl, or isopropyl; and Y is a halogen.

If $R_3$ comprises a protecting group, it can be cleaved. Similarly, a protecting group Z can be cleaved. Cleavage of a protecting group is dependent on the nature of the protecting group. For example, an acyl protecting group can be removed by treating the protecting group with acids such as hydrochloric acid, acetic acid, dilute sulfuric acid, and the like; and bases such as sodium hydroxide, potassium hydroxide, sodium methoxide, potassium methoxide, sodium ethoxide, and potassium ethoxide. Other examples of removing protecting groups can be found in "Protective Groups in Organic Synthesis, 3$^{rd}$ Edition" by Peter G. M. Wuts and Theodora W. Greene, Wiley-Interscience, 1999, which is incorporated herein by reference.

$R_1$, $R_6$, and $R_9$ can optionally be hydrolyzed from the amino acid product. Typically, hydrolysis is achieved by reacting the ester form of an amino acid with a sufficient quantity of acid or base to remove $R_1$, $R_6$, or $R_9$. The acid or base used for hydrolysis preferably does not react with or cleave, except to form a salt, other moieties of the amino acid.

Amino acid products, either enantiomers or diastereomers, of the above syntheses can be resolved. Typically, amino acids are resolved by forming a diastereomeric salt with an amino acid and a chiral amine. Suitable chiral amines include arylalkylamines such as (R)-1-phenylethylamine, (S)-1-phenylethylamine, (R)-1-tolylethylamine, (S)-1-tolylethylamine, (R)-1-phenylpropylamine, (S)-1-propylamine, (R)-1-tolylpropylamine, and (S)-1-tolylpropylamine. Resolution of chiral compounds using diastereomeric salts is further described in *CRC Handbook of Optical Resolutions via Diastereomeric Salt Formation* by David Kozma (CRC Press, 2001), incorporated herein by reference in its entirety.

Alternatively, 2-alkyl amino acids and functionalized derivatives thereof (e.g., esters) can be resolved by emulsion crystallization, as described in U.S. Pat. Nos. 5,872,259, 6,383,233 and 6,428,583, which are incorporated herein by reference. Briefly, emulsion crystallization is a process for separating a desired substance from an aggregate mixture. The process involves forming a three phase system, the first phase comprising the aggregate mixture, the second phase being liquid and comprising a transport phase, and the third phase comprising a surface upon which the desired substance can crystallize. A chemical potential exists for crystal growth of the desired substance in the third phase of the system, thereby creating a flow of the desired substance from the first phase through the second phase to the third phase, where the desired substance crystallizes and whereby an equilibrium of the activities of the remaining substances in the aggregate mixture is maintained between the first phase and the second phase.

In one example of emulsion crystallization, a solution of the racemic mixture is supersaturated (by either cooling, adding a solvent in which one or more components are sparingly soluble or by evaporation of the solution). Ultrasonication typically aids the process of forming an emulsion. The mixture is then seeded with crystals of the desired, optically active acid along with an additional quantity of surfactant and an anti-foaming agent. The desired product usually crystallizes out and can be separated by filtration. Further details of emulsion crystallization for an amino acid derivative can be found in Example 3.

Once the 2-alkyl amino acids or functionalized derivatives have been resolved, the desired isomer can be isolated. Typically, a (S)-2-amino acid, a salt, or an ester thereof is isolated. Preferably, (S)-2-methylcysteine or (S)-2-methylcysteine methyl ester is isolated.

Cysteine, a 2-alkylcysteine such as (S)-2-methylcysteine, or a cysteine alkyl ester can be coupled to a substituted or unsubstituted aryl nitrile such as a substituted or unsubstituted benzonitrile. Preferably, the substituents on benzonitrile will not interfere with the coupling reaction. In a preferred embodiment, (S)-2-methylcysteine is coupled to 2,4-dihydroxybenzonitrile to form 4,5-dihydro-2-(2,4-dihydroxyphenyl)-4-methylthiazole-4(S)-carboxylic acid (also known as 4'-hydroxydesazadesferrithiocin).

Typically, coupling of cysteine, a 2-alkylcysteine, or a cysteine alkyl ester and a substituted or unsubstituted benzonitrile includes converting the benzonitrile into a benzimidate. The benzimidate can be formed, for example, by reacting the benzonitrile with an alcohol such as methanol, ethanol, n-propanol, or isopropanol in the presence of an acid such as hydrochloric acid. Alternatively, cysteine or a related compound can be coupled directly with a benzimidate. The benzimidate is then reacted with the cysteine (or related compound) under basic conditions. Acceptable bases include trimethylamine, triethylamine, triphenylamine, dimethylamine, diethylamine, diphenylamine, diisopropylamine, diisopropylethylamine, 1,4-diazabicyclo[2.2.2]octane (DABCO), 1,5-diazabicyclo[4.3.0]non-5-ene (DBN) and the like. The reaction between the benzimidate and the cysteine results in the thiazoline (4,5-dihydrothiazole) containing product. When forming the benzimidate from a hydroxylated benzonitrile (e.g., 2,4-dihydroxybenzonitrile), the hydroxyl groups are advantageously protected (e.g., with a substituted or unsubstituted alkyl or arylalkyl group such as a benzyl group). The protecting groups are subsequently cleaved, typically by catalytic hydrogenation.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080 to Raymond J. Bergeron, Jr., the contents of which are incorporated herein by reference. Additional examples can be found in PCT/US93/10936, PCT/US97/04666, and PCT/US99/19691, the contents of which are incorporated by reference.

Suitable benzonitriles and benzimidates for use in the above coupling reaction can be synthesized by methods described in U.S. application Ser. Nos. 60/381,013, 60/380,878 and 60/380,909, all filed May 15, 2002, the entire teachings of which are incorporated herein by reference.

An alkyl group is a hydrocarbon in a molecule that is bonded to one other group in the molecule through a single covalent bond from one of its carbon atoms. Alkyl groups can be cyclic or acyclic, branched or unbranched, and saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

A cycloaliphatic group is cyclic, non-aromatic, consists solely of carbon and hydrogen and may optionally contain one or more units of unsaturation, e.g., double and/or triple bonds. A cycloaliphatic group can have one or more rings, which can be fused together. Typically, a cycloaliphatic group has one to about 24 carbons atoms, or about 1 to about 12 carbon atoms. Examples of cycloaliphatic groups include cyclopentyl, cyclohexyl, cycloheptyl, cyclooctyl, cyclodecyl, cyclopentenyl, cyclopenta-1,3-dienyl, cyclohexenyl, cyclohexa-1,3-dienyl, cyclohexa-1,4-dienyl, cycloheptenyl, cyclooctenyl, cycloocta-1,3-dienyl, and cycloocta-1,3,5-trienyl.

A heterocyclic group is a cycloaliphatic group where one or more of the carbon atoms is replaced by a heteroatom such as S, O, or N. Examples of heterocyclic groups include oxiryl, oxetyl, oxolyl, oxyl, aziridyl, azetidyl, pyrrolidyl, piperidyl, tetrahydrothiophyl, and tetrahydrothiopyryl.

Aromatic (or aryl) groups include carbocyclic aromatic groups such as phenyl, p-tolyl, 1-naphthyl, 2-naphthyl, 1-anthracyl and 2-anthracyl. Heteroaromatic groups include N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aromatic groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl and cycloaliphatic groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aromatic group. Alkyl and cycloaliphatic groups can additionally be substituted by a heterocyclic, aromatic, or heteroaromatic group (e.g. an alkyl group can be substituted with an aromatic group to form an arylalkyl group). A substituted alkyl or cycloaliphatic group can have more than one substituent.

Suitable substituents for heterocyclic, aromatic, and heteroaromatic groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aromatic group. Heterocyclic, aromatic, and heteroaromatic groups can additionally be substituted by an alkyl or cycloaliphatic group (e.g. an aryl group can be substituted with an alkyl group to form an alkylaryl group such as tolyl). A substituted heterocyclic, aromatic, or heteroaromatic group can have more than one substituent.

Functional groups of the present invention can be protected with a protecting group. For example, cysteine or a related compound is protected at one or more reactive moieties, such as at the amino, —SH, and/or carboxyl moieites of cysteine. As is known in the art, a protecting group reduces or eliminates the ability of a functional group to react with another functional group. For example, a thiol or an alcohol can be protected with an acyl group. Similarly, an alcohol can be protected by a tosyl or a trimethylsilyl group. An amine can, for example, be protected by an Fmoc group or a Boc group. Additional protecting groups, methods of adding a protecting group, and methods of removing a protecting group are taught in "Protective Groups in Organic Synthesis, 3$^{rd}$ Edition" by Peter G. M. Wuts and Theodora W. Greene, Wiley-Interscience, 1999, which was incorporated by reference above.

Protecting groups for basic nitrogen atoms include formyl; 4-toluenesulfonyl; t-butyloxycarbonyl; 2,4-dinitrophenol; benzyloxymethyl; trityl; t-butoxymethyl; 2-chlorobenzyloxy-carbonyl; allyloxycarbonyl; benzyloxycarbonyl (Z); mesitylene-2-sulfonyl; 4-methyloxy-2,3,6-trimethyl-benzyenesulfonyl; 2,2,5,7,8-pentamethyl-chroman-6-sulfonyl; 9-xanthenyl; and 2,4,6-trimethoxybenzyl.

Protecting groups for basic sulfur groups include 4-methylbenzyl; 3-nitro-2-pyridinesulfenyl; trityl; 2,4,6-trimethoxybenzyl; acetamidomethyl; trimethylacetaminomethyl; t-butylsulfonyl; and sulfoxide.

Protecting groups for basic oxide groups include benzyl ether; t-butyl ether; benzyl ether; 2,6-dichlorobenzyl ether; 2-bromobenzyl ether; and 3,5-dibromobenzyl ether.

Carboxyl groups can be protected, for example, as ethers or as carboxamides. For example, when a carboxyl group is protected as an ether, it takes the form of —COOR wherein R is a substituted or unsubstituted C1 to C10 alkyl group, a substituted or unsubstituted up to C30 alkyl group, or a substituted or unsubstituted alkyl-aryl group wherein the alkyl group is C1 to C5 and the aryl group is up to C30. When a carboxyl group is protected as a carboxamide, it takes the form of —CONR' wherein R' is —H or as in R above.

Leaving groups are typically weak bases. Suitable leaving groups include halogen, tosyl, triflyl, brosyl, p-nitrophenyl, 2,4-dinitrophenyl, and mesyl groups. Halogens include bromine, chlorine, and iodine.

Also included in the present invention are salts of the disclosed amino acids and amino acid esters (including side chains). For example, amino acids can also be present in the anionic, or conjugate base, form, in combination with a cation. Suitable cations include alkali metal ions, such as sodium and potassium ions, alkaline earth ions, such as calcium and magnesium ions, and unsubstituted and substituted (primary, secondary, tertiary and quaternary) ammonium ions. Suitable cations also include transition metal ions such as manganese, copper, nickel, iron, cobalt, and zinc. Basic groups such as amines can also be protonated with a counter anion, such as hydroxide, halogens (chloride, bromide, and iodide), acetate, formate, citrate, ascorbate, sulfate or phosphate.

EXAMPLE 1

A one-necked, 100 mL, round-bottomed flask was fitted with Dean-Stark apparatus attached with a drying tube (CaCl$_2$) and a magnetic stirrer. The flask was charged with 5 g (26.6 mmol) of t-butyl ethyl malonate, 2.39 g (78.8 mmol) of formalin solution (35% formaldehyde in water), 3.4 g (40 mmol) of piperidine and 50 mL of toluene. The mixture was heated to reflux with stirring in an oil bath at 120–130° C. for 8 hours. After cooling to room temperature, toluene was removed under reduced pressure. The crude oily product was purified by column chromatography on silica gel, and was eluted with ethyl acetate/petroleum ether (6:94) to give 3.56 g (67%) of t-butyl ethyl methylene malonate.

$^1$H NMR (CDCl$_3$, 200 MHz) δ 1.35 (t, 3H), 1.55 (s, 9H), 4.30 (q, 2H), 6.40 (d, 2H).

To a one necked 50 mL round-bottomed flask fitted with a reflux condenser and an outlet dipped inside aqueous KMnO$_4$ solution, 1.0 g (5 mmol) of t-butyl ethyl methylenemalonate and 1.4 g thiol acetic acid (18.4 mmol) was heated under reflux for 12 hours. The mixture was allowed to cool, and the product was purified by silica gel column chromatography using ethyl acetate/petroleum ether (7:93) to afford 0.86 g (62%) of t-butyl ethyl acetylthiomethylmalonate as a colorless liquid.

$^1$NMR (CDCl$_3$, 200 MHz) δ 1.35 (t, 3H), 1.50 (s, 9H), 2.35 (m, 3H), 2.52 (m, 2H), 3.30 (m, 1H), 4.20 (m, 2H).

EXAMPLE 2

Methyl t-butyl 2-methylidenyl-1,3-dipropionate is reacted with thioacetic acid to form methyl t-butyl 2-acetylthiomethyl-1,3-dipropionate. Methyl t-butyl 2-acetylthiomethyl-1,3-dipropionate is alkylated with potassium carbonate and methyl iodide in the presence of a phase transfer catalyst to form methyl t-butyl 2-acetylthiomethyl-2-methyl-1,3-dipropionate. The t-butyl group is hydrolyzed by acidifying the reaction mixture. The free carboxylic acid group produced by hydrolyzing the t-butyl group is converted to an amino group through a reaction with diphenylphosphoryl azide, thereby forming S-acetyl-2-methylcysteine methyl ester. The acetyl group is removed to form 2-methylcysteine methyl ester.

EXAMPLE 3

All compounds were used without further purification. The surfactants Rhodafac RE610 and Soprophor FL were obtained from Rhône-Poulenc, Surfynol 465 from Air Products, Synperonic NP 10 from ICI and sodium lauryl sulfate from Fluka. For agitation a shaking machine was used (Buhler KL Tuttlingen). Purities of the resulting crystals were measured by using a PolarMonitor polarimeter (IBZ Hannover). Ethanol was used as the solvent. The total crystal quantity was dissolved in a 1 mL cell at 20° C.

45 mg of (R,R)— and (S,S)—amino acid derivatives were dissolved in 1 ml of a mixture of 20% v/v 2-hexanol, 12% v/v Rhodafac RE 610, 6% v/v Soprophor FL and 62% v/v water by heating to 80° C. in a 5 mL vial. After the organic derivative was completely dissolved the microemulsion was cooled down to room temperature and agitated using a shaking machine (420 rpm). During two hours no spontaneous crystallization was observed. The mixture was then seeded with two drops of a dilute, finely ground suspension of pure (S,S)—(-) amino acid or its ester crystals grown under similar conditions. After 2 hours of agitation the resulting crystals were filtered off, washed with water and dried in a gentle nitrogen stream.

EXAMPLE 4

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallisation was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S entantiomer.

EXAMPLE 5

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 ml concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4 (S)-carboxylic acid product. $^1$H-NMR showed no significant impurity.

EXAMPLE 6

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to -5° C., stirred and saturated with dry HCl gas over 5 hours at 0–3° C. The reaction mixture was stirred overnight at 2–4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a compound represented by Structural Formula (I):

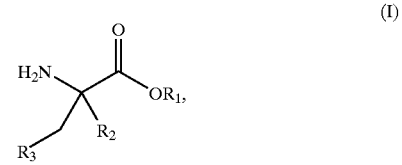

or a salt thereof
wherein:
$R_1$ is —H or a substituted or unsubstituted alkyl group;
$R_2$ is a substituted or unsubstituted alkyl group; and $R_3$ is —H, —SH, —OH, —NH$_2$, —CO$_2$H, —CONH$_2$, —NHC(NH)NH$_2$, a substituted or unsubstituted alkyl group, a substituted or unsubstituted cycloaliphatic group, or a substituted or unsubstituted aromatic group, wherein $R_3$ optionally comprises a protecting group;

comprising the steps of:

a.) reacting a nucleophile of the formula A—$R_3$ or A—($R_3$)$_2$ with a compound represented by Structural Formula (II):

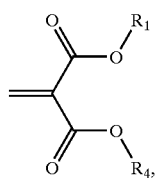
(II)

wherein:
A is —H, —Li,

—CuLi,

—MgCl, —MgBr, or —MgI, provided that A and $R_3$ are not each —H;

$R_4$ is —H or a substituted or unsubstituted alkyl group; and $R_1$ and $R_3$ are as defined above;

thereby forming a compound represented by Structural Formula (III):

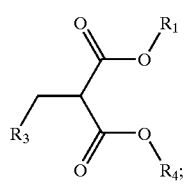
(III)

b.) reacting the compound represented by Structural Formula (III) with one or more bases, $R_2X$, and a phase transfer catalyst, wherein X is a leaving group; and $R_1$, $R_2$, $R_3$, and $R_4$ are as defined above; thereby forming a compound represented by Structural Formula (IV):

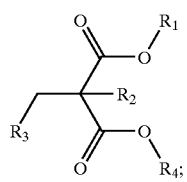
(IV)

c.) converting the compound represented by Structural Formual (IV) into a compound represented by Structural Formula (V):

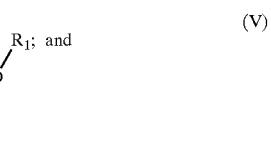
(V)

d.) optionally cleaving the protecting group of $R_3$, thereby forming the compound represented by Structural Formula (I).

2. The method of claim 1, wherein in step (c.), the compound represented by Structural Formula (IV) is reacted with a source of azide and water.

3. The method of claim 2, wherein the source of azide is MN$_3$ or diphenylphosphoryl azide, wherein M is H or an alkali metal.

4. The method of claim 1, wherein step (c.) comprises amidating the compound represented by Structural Formula (IV) to an amide represented by Structural Formula (VI):

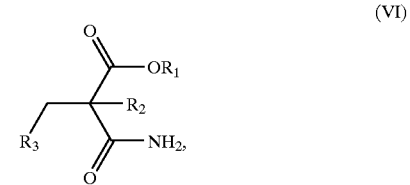
(VI)

and reacting said amide with:
1.) MOR$_5$ and (Y)$_2$, or
2.) MOY;

wherein M is an alkali metal; $R_5$ is hydrogen, methyl, ethyl, propyl, or isopropyl; and Y is a halogen.

5. The method of claim 3, wherein $R_2$ in Structural Formulas (I), (IV) and (V), and $R_2X$ is a C1–C4 alkyl group and X in $R_2X$ is a halide.

6. The method of claim 5, wherein $R_3$ is —H, —(CH$_2$)$_x$S(CH$_2$)$_y$H, —(CH$_2$)$_x$O(CH$_2$)$_y$H, —(CH$_2$)$_x$NH(CH$_2$)$_y$H, —(CH$_2$)$_x$C(O)NH$_2$, —(CH$_2$)$_x$C(O)OH, —(CH$_2$)$_x$NHC(NH)NH$_2$, a C1–C6 substituted or unsubstituted alkyl group,

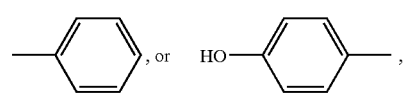

wherein $R_3$ optionally comprises a protecting group;
x is an integer from 0–6; and
y is 0 or 1.

7. The method of claim 6, wherein $R_3$ is —SH.

8. The method of claim 6, further comprising the step of resolving the enantiomers or diastereomers of the compound represented by Structural Formula (I).

9. The method of claim 8, further comprising the step of isolating an (S)-2-amino acid or an ester thereof from the diastereomers or enantiomers of the compound represented by Structural Formula (I).

10. The method of claim 1, wherein $R_1$ is methyl and $R_4$ is t-butyl.

11. The method of claim 10, wherein in step (c.), the compound represented by Structural Formula (IV) is reacted with a source of azide and water.

12. The method of claim 11, wherein the source of azide is $MN_3$ or diphenylphosphoryl azide, wherein M is H or an alkali metal.

13. The method of claim 12, wherein $R_2$ in Structural Formulas (I), (IV) and (V), and $R_2X$ is a C1–C4 alkyl group and X in $R_2X$ is a halide.

14. The method of claim 13, wherein $R_3$ is a bond, —$(CH_2)_xS(CH_2)_yH$, —$(CH_2)_xO(CH_2)_yH$, —$(CH_2)_xNH(CH_2)_yH$, —$(CH_2)_xC(O)NH_2$, —$(CH_2)_xC(O)OH$, —$(CH_2)_xNHC(NH)NH_2$, a C1–C6 substituted or unsubstituted alkyl group,

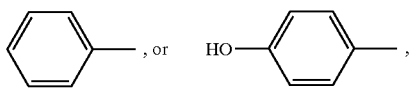

wherein $R_3$ optionally comprises a protecting group;
x is an integer from 0–6; and
y is 0 or 1.

15. The method of claim 14, wherein $R_3$ is —SH.

16. The method of claim 15, further comprising the step of resolving the enantiomers or diastereomers of the compound represented by Structural Formula (I).

17. The method of claim 16, further comprising the step of isolating an (S)-2-amino acid or an ester thereof from the enantiomers or diastereomers of the compound represented by Structural Formula (I).

* * * * *